(12) United States Patent
Stein et al.

(10) Patent No.: US 8,916,097 B2
(45) Date of Patent: Dec. 23, 2014

(54) CONTROLLER FOR AUTOMATED IMMUNOASSAY SYSTEM

(75) Inventors: David Stein, Succasunna, NJ (US);
Marcel J. Goetz, Jr., Saylorsburg, PA (US); Sanchoy Das, Bridgewater, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 3378 days.

(21) Appl. No.: 10/813,587

(22) Filed: Mar. 31, 2004

(65) Prior Publication Data
US 2005/0220671 A1    Oct. 6, 2005

(51) Int. Cl.
G01N 21/00 (2006.01)
G01N 35/02 (2006.01)
G01N 35/00 (2006.01)
G01N 33/00 (2006.01)
G01N 31/00 (2006.01)

(52) U.S. Cl.
CPC ................................. G01N 35/0092 (2013.01)
USPC .................. 422/67; 422/62; 422/63; 422/64; 422/65; 422/66; 436/50; 436/55

(58) Field of Classification Search
USPC ............................................................ 422/67
See application file for complete search history.

(56) References Cited

U.S. PATENT DOCUMENTS

| 5,316,726 | A | 5/1994 | Babson et al. | |
|---|---|---|---|---|
| 5,972,295 | A * | 10/1999 | Hanawa et al. | 422/65 |
| 7,175,334 | B2 | 2/2007 | Babson et al. | |
| 7,951,329 | B2 | 5/2011 | Malyarov et al. | |
| 8,215,821 | B2 | 7/2012 | Babson et al. | |

* cited by examiner

Primary Examiner — Neil N Turk
(74) Attorney, Agent, or Firm — Novak Druce DeLuca & Quigg LLP

(57) ABSTRACT

A controller for an automated immunoassay system is provided to manage the system resources and control the flow of samples under test. The controller allows tests to be run dynamically instead of in a serial, first in first out flow. The controller evaluates the set of tests to be run and generates a sequencing strategy. The sequencing strategy is based on the paths specified for each type of assay, the numbers of tests to be run, the priority of each test and the resources required for each test. In addition, the controller can resolve resource allocation conflicts and modify the sequencing strategy as test conditions change during operation.

20 Claims, 12 Drawing Sheets

Historical Saturation Level Procedure

CONTROLLER FOR AUTOMATED IMMUNOASSAY SYSTEM

BACKGROUND OF THE INVENTION

1. Field of the Invention

The present invention generally relates to controller within an automated immunoassay analyzer used to manage the multipath flow of test samples through an automated immunoassay analyzer, and, more particularly to automatically accept, identify, schedule, allocate resources, and measure test samples so as to maximize the throughput of the automated immunoassay analyzer.

2. Background Description

Automated immunoassay analyzers are being manufactured that allow a computer controlled system to analyze the amount of analyte in a sample such as blood, plasma or urine. To quantify the results, the sample is subjected to a myriad of complex processes that may include sample dilution, adding reagents, incubating, agitating, washing and reading of the sample. Reading of the sample is performed using a detection mechanism (e.g., chemiluminescent) that measures the intensity of the light and calculates the related value of the analyte. See for example U.S. Pat. No. 5,885,530; U.S. Pat. No. 5,885,529; U.S. Pat. No. 5,723,092; U.S. Pat. No. 5,721,141; U.S. Pat. No. 5,632,399; U.S. Pat. No. 5,318,748; U.S. Pat. No. 5,316,726; U.S. Pat. No. 5,258,309; U.S. Pat. No. 5,098,845; U.S. Pat. No. 5,084,240; and U.S. Pat. No. 4,639,242; all of which are herein incorporated by reference.

Automated immunoassay analyzers have traditionally performed testing of samples in a serial manner. For example, a sample is presented to the analyzer and it progresses step by step through the various processes until completion. While this first sample is progressing through the analyzer, all other samples follow. That is, there is a single path through currently available analyzers. This means the tests must be performed in a serial fashion on a first come first serve basis, see for example, Babson et al. (U.S. Pat. No. 5,885,530) which is herein incorporated by reference.

Furthermore, throughput of immunoassay analyzers can be impacted by the access to samples for test. Automating the loading and unloading of the samples reduces the amount of operator attention necessary to complete the testing. The more samples that can be stored, loaded, tested, and unloaded from the analyzer without operator intervention, the more efficient the instrument can be.

Duration of individual tests are not consistent for each of the different types of tests that can be performed. Some samples need to be diluted before the reagent is added. Other tests require two different reagents, and still other tests need longer incubation times. To progress these tests on a serial immunoassay analyzer, the best throughput is predicated on the time duration of the longest test in the system. This can significantly impact the throughput of other less time consuming tests.

Furthermore, interruption of a test schedule to insert higher priority tests requires tests in processes to be halted and the higher priority tests to be loaded and run. This requires both significant operator intervention and adversely effects the tests currently being performed in that they may be destroyed or the results compromised.

SUMMARY OF THE INVENTION

It is an object of this invention to provide a dynamic controller for an automated immunoassay analyzer.

It is another object of this invention to provide dynamic resource allocation that optimizes the use of each subsystem of the automated immunoassay analyzer and processes tests more efficiently.

It is still another object of the invention to dynamically control the automated immunoassay analyzer to perform high volume testing on a broad range of analytes while selecting from among a diverse set of immunoassays.

It is a further object of the invention to define and allocate testing resources for each immunoassay to be performed.

It is another object of the invention to achieve high throughput of the automated immunoassay analyzer preferably up to or exceeding 200 test results per hour.

It is still another object of the invention to perform the immunoassays without operator intervention once the samples are loaded into the automated immunoassay analyzer.

Another object of the invention is to manage the schedule of tests and allocation of resources based on customer selection of saturation thresholds to allow sufficient opportunity to insert high priority tests without halting tests in process.

It is still another object of the invention to enable the scheduling of resources and the launching of tests to adapt to predicted levels of saturation based on historical information 'learned' by the dynamic controller.

It is still a further object of the invention to allocate resources for testing to balance the workload across duplicate resources to reduce maintenance and repair times.

According to the invention, the dynamic controller is a processor based system that accepts operator input via a keyboard and/or mouse to define the tests to be conducted. A bar code reader, RF tag, or other means for identifying the samples can be used to associate the desired tests with the specific samples to be tested. The dynamic controller will calculate test sequences for each of the samples based on resource and timing requirements and will launch the tests in an optimized sequence. The dynamic controller will be able to set resource saturation levels in response to user input or based on predicted saturation levels determined from historical data.

Furthermore, the dynamic controller of the present invention permits accessing the samples in a randomized fashion, as opposed to a serial, one after the other, fashion. This allows for a controller to manage the varying time periods between entering samples into the analyzer instrument for testing and processing the samples through the selected assays. In this way, the time durations for the various types of tests being performed can be optimized.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
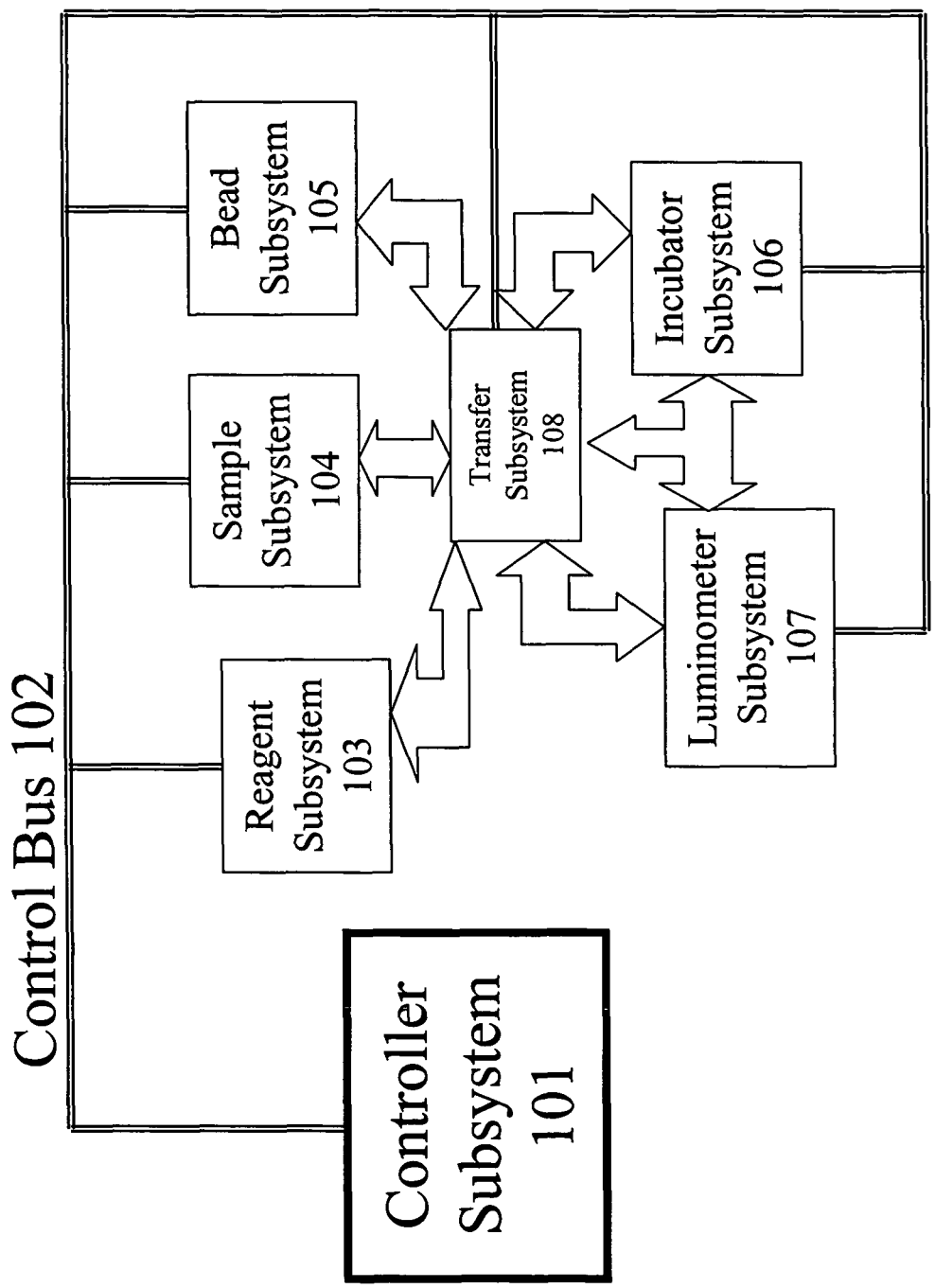
FIG. 1 is an overview of an automated immunoassay analyzer.

In one embodiment, the present invention provides a controller for an immunoassay analyzer that allows immunoassay tests to be performed in a controlled multiple path manner rather than in a "first in, first out" (FIFO) serial process. In the controller of the present invention, a sample in a test vessel or a group of samples in a group of test vessels can follow one of a number of pathways that are individually tailored to carry out the physical manipulations (e.g. dilution, mixing, emptying, etc.) and chemical reactions (e.g., by addition of chemical reactants) on a separate schedule for each particular assay. This is accomplished without interfering with (e.g., slowing down) the reactions and manipulations that other samples in the incubator are undergoing, such as an entirely different assay, or for the same assay but under different conditions. For example, with the controller of the present invention, it is possible to incubate and process at the same time and in the same analyzer, one group of 20 samples with an assay procedure requiring: sample dilution, addition of reagent, 2 minutes of incubation, and reading of the assay result; and a second group of 12 samples requiring: no sample dilution, addition of reagent, 5 minutes of incubation, emptying of test vessel and washing of the sample, addition of second reagent, second incubation of 10 minutes, emptying of test vessel and washing of the sample, and reading of the assay result. Further, it would be possible to simultaneously carry out a single type of assay with 50 test vessels, subsets of which are incubated for increased lengths of time (e.g., the first 10 samples are incubated for 5 minutes, the second 10 are incubated for 10 minutes, and so on). These variations can be accomplished by preprogramming the desired pathways and, in contrast to conventional incubators, do not require the intervention of a technician when switching from one pathway to another, and do not require that the pathway for one group of assays be completed prior to beginning the pathway for another group of assays. Further, the assays can be carried out without regard to what order the requested assays were entered into the analyzer.

The controller also enables the resource allocation to be controlled so as to ensure resource availability of resources for testing (e.g., incubator chain space, wash station, luminometer chain, detection mechanism, etc.) in the event of higher priority (e.g., STAT) tests to be performed. Specifically, higher priority tests can be launched at anytime and the controller of the present invention can schedule processing of these new high priority tests while continuing to manage the progress of those samples currently under test and those scheduled for testing but not yet launched. Current immunoassay analyzers require that the test process be interrupted, samples currently under test be disposed, and the high priority test or tests be run and all other test samples wait until the high priority tests are completed. The present invention provides a resource saturation capability to ensure high priority tests can be introduced and processed without disrupting or losing the sample currently under test.

Referring now to the drawings, FIG. 1 shows an automated immunoassay analyzer as a complex system with numerous subsystems that allow tests to be performed without the continuous monitoring and intervention of a technician. The controller subsystem 101 selects the tests to be performed for each sample from the Automated Laboratory Information System (LIS). The technician may enter test selection data, however, the preferred embodiment is to select tests through the LIS. The controller subsystem 101 manages the other subsystems by sending command and control information via the control bus 102. Samples of biological material (e.g., urine, plasma, etc.) are placed by the technician in the sample subsystem 104. The samples can be diluted within the sample subsystem 104 or can be tested in the undiluted state. The bead subsystem 105 adds the appropriate bead (e.g., a substrate with bound agent for binding an analyte of interest in the sample) to the test vessel and the reagent subsystem 103 adds the specified reagent to the test vessel. The selection of bead and reagent for each sample is managed by the controller subsystem 101 based on the type of test to be performed on each sample. These subsystems include identification capabilities such as bar code readers or RF tag readers that read the identification information on the reagent containers, bead containers and test vessels to ensure that correct components are added to each test vessel for testing. The test vessel is moved within the analyzer via the transfer subsystem 108. Once the selected components are added to the test vessel, the incubator subsystem 106 incubates and agitates the test vessel as managed by the controller subsystem 101. The test vessel is then washed and transferred to the luminometer subsystem 107 via the transfer subsystem 108. The luminometer subsystem 107 selects the test vessel and presents it to a detection mechanism. After the read operation is performed, the test vessel is discarded.

Figure 2:
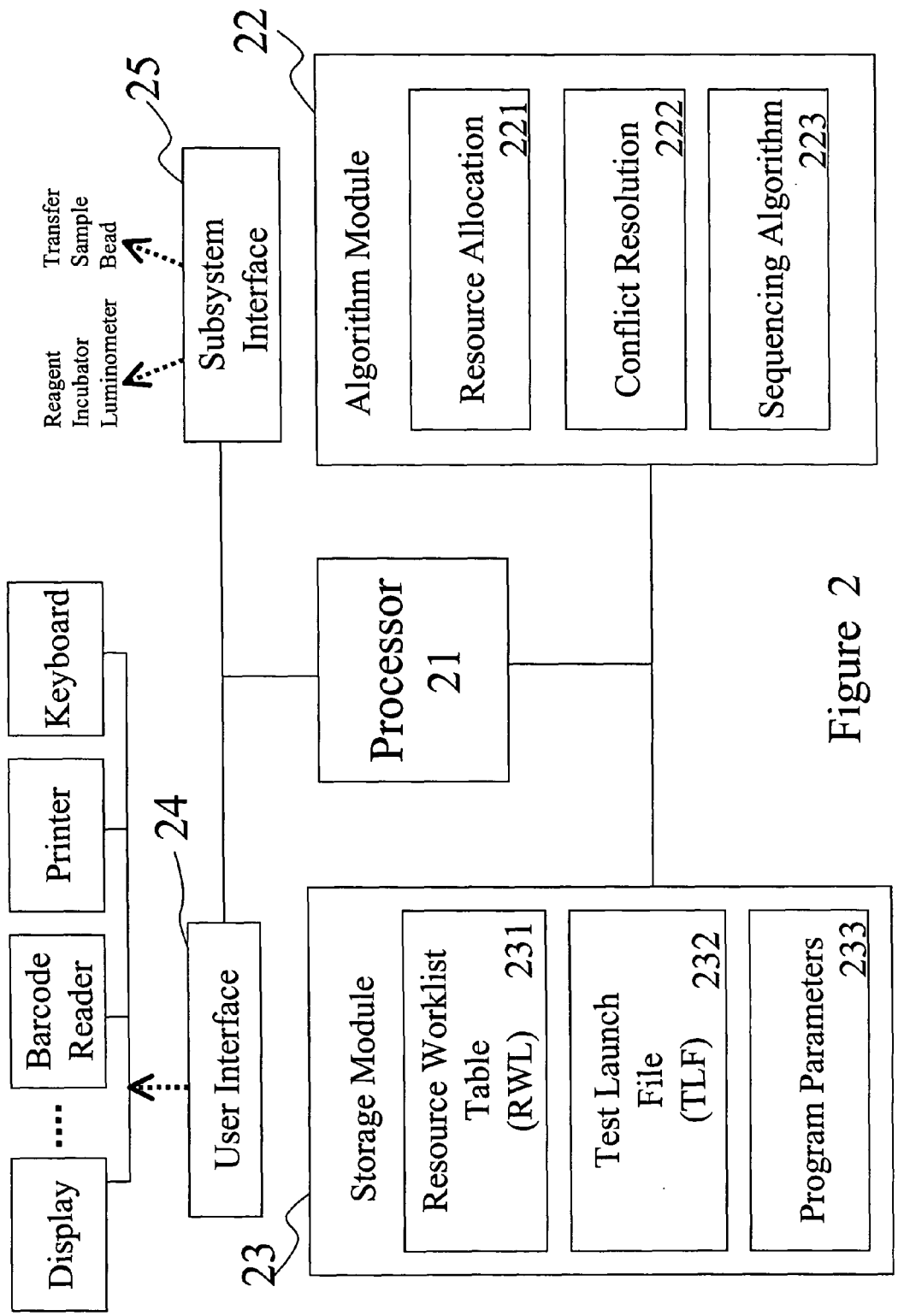
FIG. 2 is a block diagram of the major elements associated with dynamic controller.

The present invention is directed to a controller subsystem of the automated immunoassay analyzer. Referring now to FIG. 2, the controller includes a processor 21 which is a computer based software and hardware implemented element used to control and monitor the flow of test samples through the analyzer. The test data, such as test types, test paths, resource utilization and other related information is entered into the controller via the user interface 24 using anyone of several input devices such as bar code reader, keyboard, mouse, etc. In addition, the controller will display test results and status information on any one of several output devices to include but not limited to a video display, printer, etc. Test components such as test samples, reagents, etc. are entered into the system and managed by the controller through the subsystem interface 25. Test data entered via the user interface 24 and the subsystem interface 25 or generated by the controller algorithms are stored within the controller storage module 23. Test data variables used to form the vectors within the immunoassay process are entered into a database and stored within the storage module as program parameters 233. A list of some of the program parameters 233 are provided in Table 1.

TABLE 1

| Program Parameters | |
|---|---|
| K | Test ID#. Assigned sequentially as test is assigned to patient sample |
| t | Current Instrument Cycle # |
| T | Instrument Cycle # of last test launched |
| N | Number of tests to be launched |
| P(K) | Assigned path through which test will be processed |
| $T_{11}(K)$ | Target $1^{st}$ Incubation on Belt 1 |

TABLE 1-continued

Program Parameters

| | |
|---|---|
| $T_{12}(K)$ | Target $1^{st}$ Incubation on Belt 2 |
| $T_1(K)$ | Total $1^{st}$ Incubation Time |
| $T_{21}(K)$ | Target $2^{nd}$ Incubation on Belt 1 |
| $T_{22}(K)$ | Target $2^{nd}$ Incubation on Belt 2 |
| $T_2(K)$ | Total $2^{nd}$ Incubation Time |
| $Q_1(t)$ | Number of filled positions on Belt 1 |
| $Q_2(t)$ | Number of filled positions on Belt 2 |
| E | Test Profile Data including required resources; Priority, Reagent Pipetting, Sample Pipetting, Incubation Times, Washing, Pretreatment Steps, Dilution and Dilution factor |

Once test samples have entered the analyzer, the controller initiates the sequence algorithm 223. The sequence algorithm 223 begins assigning specific test paths to each test sample and to distribute the incubation times across the available incubator chains.

The resource allocation algorithm 221 generates the resource worklist table 231 based on the specific path each test sample will follow which is then stored in the storage module 24. Once the sequence algorithm is initiated and the resource worklist table 231 is completed, the test launch file 232 is generated. This test launch file 232 is a list of the tests waiting to be launched. During the test process, the controller monitors the operation of the analyzer for resource conflicts using a resource resolution algorithm 222. This algorithm ensures that, as new tests are scheduled for launch, either standard tests or priority tests, the system resources will be available at the appropriate cycle times.

Figure 3:
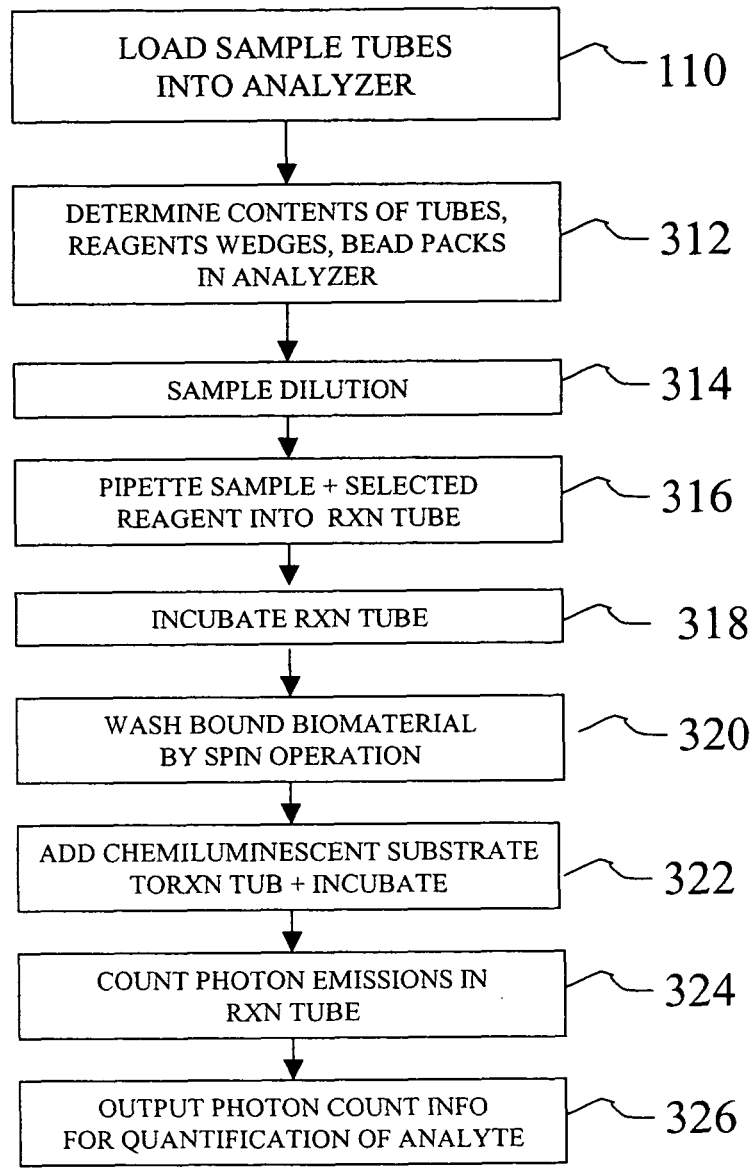
FIG. 3 is a flow diagram that describes the serial test procedures of current immunoassay analyzers. (Prior Art)

In order to more completely understand the operation of the dynamic controller, it is useful to review the operation of existing analyzer control processes. As shown in FIG. 3, the test process begins with step 110 when a sample tube is loaded into the analyzer. The controller then identifies the various test components (e.g., tube contents, reagent identification, and bead selection, etc.) in step 312. The test dilution is then performed in step 314 followed by pipetting of sample and reagent into the test vessel at step 316. The test vessel is then incubated at 318. When incubation is complete, step 320 performs the washing and then the substrate is added to the test vessel at step 322. The measurement is taken at step 324 and finally the results are displayed at step 326. This process takes each test in its turn and progress through the process until complete. it does not allocate resources to perform other operations while waiting for the current test vessel to cycle through the process.

Figure 4:
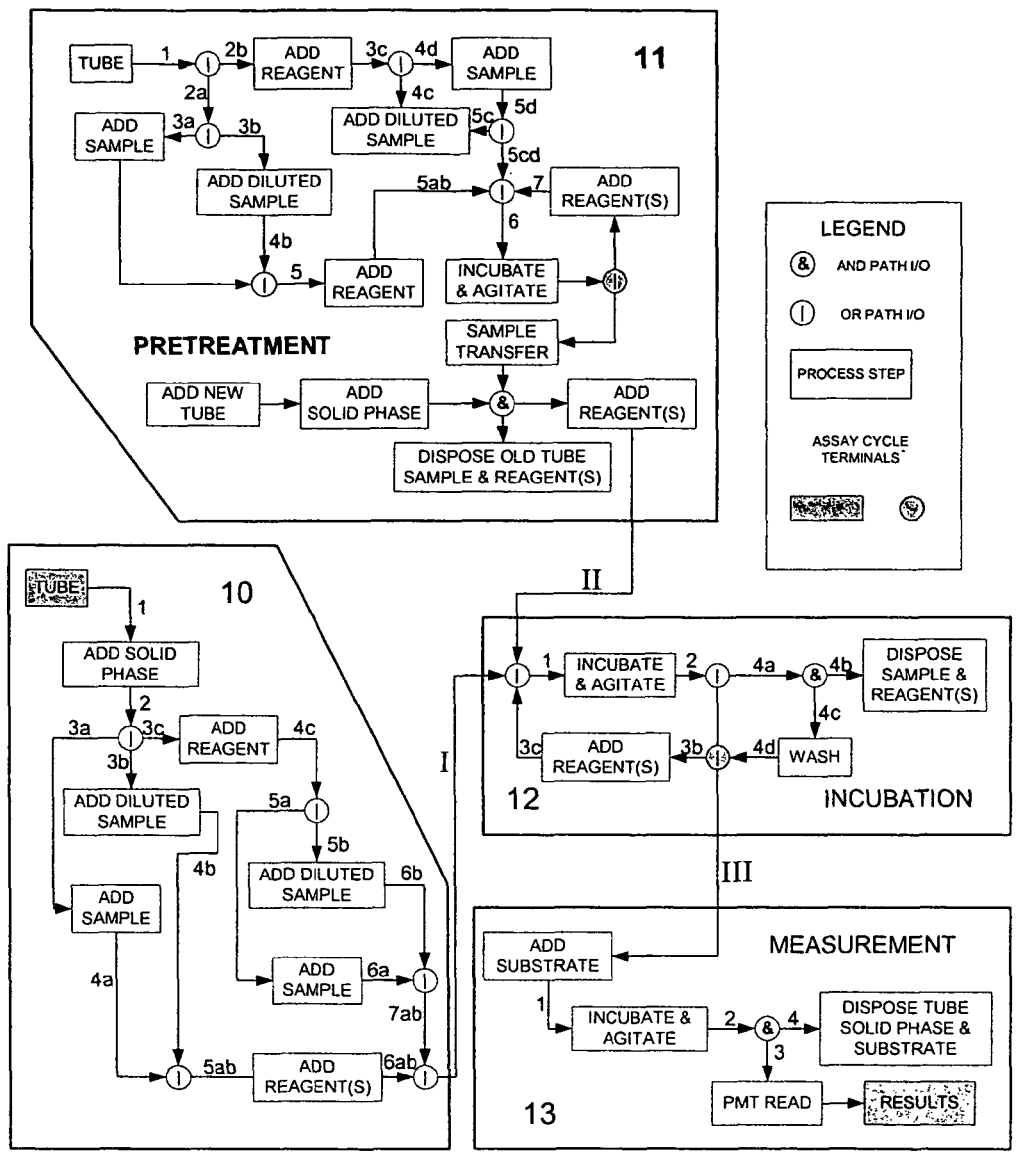
FIG. 4 is a schematic depiction of processes for carrying out assays according to the present invention, shown as a series of flow charts.

The existing process described by FIG. 3 is in contrast to the process controlled by this invention. The test process controlled by the present invention preferably operates in a manner that is depicted schematically as a series of flow charts in FIG. 4, where the flow chart in pentagon 10 represents a standard assay procedure, the flow chart in pentagon 11 represents a pretreatment assay process, the flow chart in rectangle 12 represents an incubation process, and rectangle 13 represents a measurement process. The processes are linked to one another and are carried out by algorithms that allow a choice of the identity, order and timing of the steps of an assay. The resource allocation algorithm 221 is utilized in order to maximize throughput on the instrument. The various sub-schemes can be conveniently understood by considering them one by one. In each schematic process, the steps of the process are given inside the small rectangles located within the flow chart. The pathways for moving from one step to another are represented by arrows, and will typically coincide with physical movement of a sample tube from one section of the instrument to another (e.g. from a pipetting station to a transfer or wash station) by means of a transport device such as an incubator belt. In each of the schematic processes, a "circle containing a vertical line" represents an "or" junction. An "or" junction is a nexus in the process which may be arrived at or exited from by more than one input or output (I/O) path, i.e., it is a point of connection in the process where a choice must be made between various options, or where a choice between various options was made in order to arrive at the junction. This is in contrast to the junctions marked with a "circle with a &", i.e. the "and" junctions. For "and" junctions, all of the possible input and output paths (represented by arrows) to and from that junction must occur. Terminal process steps are indicated by shading of the corresponding rectangle.

A. Standard Assay Process: Pentagon 10

The sub-scheme shown in Pentagon 10 represents a standard assay process. In the sub-scheme, an assay tube that is entering the assay process is represented by the shaded rectangle in the upper left corner of the pentagon 10 that is labeled "tube". This represents the beginning of the standard assay process illustrated in Pentagon 10. The arrow 1 leaving the tube leads to the first step of the process, which is "add solid phase". In other words, in this standard assay process, the first step is to add to the assay tube a solid phase that is relevant to the assay that is being carried out. In preferred embodiments, such a solid phase might be, for example, a bead to which an antibody molecule is attached. (A more detailed discussion of solid phases is given below.) Following this step, the arrow 2 leads to an "or" junction from which any one of three different pathways (3a, 3b or 3c) may be pursued. If pathway 3a is selected, the next step in the assay is to "add sample". If pathway 3b is selected, the next step is to "add diluted sample". Lastly, if pathway 3c is selected, the next step is to "add reagent" to the tube. Examples of suitable samples and reagents for utilization in the practice of the present invention are discussed below.

Those of skill in the art will recognize that this first tier of choices (arrows 3a, 3b and 3c) is designed to accommodate a variety of common assay strategies: the use of undiluted sample directly to a solid phase reagent, the dilution of the sample prior to addition to the solid phase, and the addition of one of more additional reagents to the solid phase prior to sample addition, all of which can be accomplished in a single analytical instrument.

Pathways 3a and 3b then proceed via arrows 4a and 4b, respectively, to a second "or" junction. (This is an "or" junction because two possible pathways lead to it, either of which may have been followed). For both 4a and 4b, there is a single pathway leading from the "or" junction, pathway 5ab, which leads to the step of the addition of one or more reagents to the assay tube. This is reasonable because both assay tubes from both the 4a and 4b pathways already contain all other requisite assay components: 1) sample, either diluted or not; and 2) solid phase reagent. Then, having added the one or more reagents, assay tubes from the 5ab pathway follow arrow 6ab to the last "or" junction of the standard assay procedure and are ready to begin the next phase of the assay (incubation) by following the arrow marked as "I".

Pathway 3c is essentially the reciprocal of 3a and 3b. Having first added one or more reagents, the sample (either diluted or not) is afterwards added to the assay tube. This is accomplished by following arrow 4c to the junction at which the choice is made between adding sample without dilution (arrow 5a) or adding diluted sample (arrow 5b). The addition of sample to the assay tubes is the last step prior to following arrows 6a and 6b to the final "or" junction. The 3c pathway assay tubes now contain all necessary assay components, and are ready to move via arrow 7ab to the last "or" junction, which they share with the 3a and 3b pathway samples. They can then proceed to the incubation phase of the assay via arrow I.

As can be seen, tubes that arrive at the final "or" junction in sub-scheme 10 just prior to incubation may have followed any of four different pathways: 1) addition of undiluted sample followed by reagent addition; 2) addition of diluted sample followed by reagent addition; 3) addition of reagent followed by addition of undiluted sample; and 4) addition of reagent followed by addition of diluted sample. In a conventional analyzer, such variation in assay pathways would require lengthy serial incubations and/or frequent intervention by the technical operator. In the present invention, such multiple assay pathways with differing requirements may be pursued at the same time in the same instrument after a single initiation procedure/start time, or after multiple start times, at the convenience of the operator.

B. Pretreatment: Pentagon 11

Pentagon 11 represents a sub-scheme into which pretreatment of a sample has been programmed. Referring to pentagon 11, multiple pathways can also be traced through the flow chart presented therein. In this case, the sample is pretreated prior to being added to the solid phase and reagents that are needed for the ultimate assay. An example of the need for pretreatment is an assay for vitamin B12 in which the analyte must be released from endogenous binding proteins in serum with a reducing agent prior to reactions involving the solid phase. Beginning with the assay tube depicted in the upper left hand corner, as is the case for the assay in pentagon 10, there are four pathways that may be followed: 1) the addition of sample followed by addition of reagent (arrows 2a, 3a, 4a, and 5); 2) the addition of diluted sample followed by addition of reagent (arrows 2a, 3b, 4b, and 5); 3) the addition of reagent followed by the addition of sample (arrows 2b, 3c, 4d, 5d, 5cd, and 7); and 4) the addition of reagent followed by the addition of diluted sample (arrows 2b, 3c, 4c, 5c, 5cd, and 7). All four paths converge at an "incubate and agitate" step, (immediately following arrow 6) which is then followed by an "or" junction. At the "or" junction, either additional reagents may be added (followed by reincubation and agitation and return to the same "or" junction), or the sample may be transferred to the next stage of the process ("sample transfer"). If sample transfer occurs, the assay proceedings arrive at an "and" junction where the contents of the assay tube are transferred to a new tube (which already contains a suitable solid phase reagents for carrying out the assay for the product are added, and the old tube is disposed of. The assay tube and contents are then ready to be transferred to the incubation phase of the assay via arrow II.

Assays requiring such different steps may carried out simultaneously. Further, multiple assays as described in the sub-schemes depicted in Pentagons 10 and 11 may be carried out simultaneously in the same analyzer.

C. Incubation Phase: Rectangle 12

Upon entry into the incubation phase of the assay system, all assay tubes from all pathways pass through a first "or" junction to a step of incubation and agitation via arrow 1. Those of skill in the art will recognize that the time of incubation may vary widely from assay to assay. Depending on the particulars of an assay, the time of incubation may be in the range of a few minutes to several hours. An advantage of the present invention is that by dynamically controlling the resources for testing and the samples under test, assays with differing incubation time requirements may be carried out simultaneously in the same assay instrument.

Upon completion of incubation and agitation, the assays proceed to an "or" junction by following arrow 2. At this "or" junction, a choice is made between 1) the addition of additional reagents to the assay (via arrows 3a and 3b; or 2) the step of sample and reagent disposal, and washing of the solid phase via arrows 4a, 4b and 4c. If the latter path is chosen, after a washing step and arrival at an "or" junction via arrow 4d, it is possible either to add additional reagents and re-incubate (arrows 3b and 3c), or to exit the incubation phase and enter the measurement phase by following arrow III. If the former path is chosen, eventually, after sufficient steps of adding reagents, incubating and washing, the assay will be complete and ready to enter the measurement phase via arrow III.

D. Measurement Phase: Rectangle 13

In the measurement phase of the assay, the amount of analyte of interest is quantified. As illustrated in rectangle 13, a suitable substrate and/or chemical reagent is added to the assay tube, the tube (via arrow 1) is incubated with agitation for an appropriate amount of time, and (via arrows 2 and 3) the resulting signal is read using a photomultiplier tube (PMT) whilst tube disposal is carried out via arrow 4. In preferred embodiments, chemiluminescent techniques are used to quantify the analyte.

Those of skill in the art will recognize that many types of assays are amenable to being carried out advantageously utilizing the present invention. In preferred embodiments, the assays are immunoassays. Some general test categories include but are not limited to those directed to thyroid function, hormones, tumor markers, infectious diseases, allergy testing, detection of proteins and/or peptides and fragments thereof [e.g., immunoglobulin and related proteins and peptides, or prostrate specific antigen (PSA)], steroids; drugs and other small molecules (e.g. therapeutic drugs and/or drugs of abuse); vitamins; various biochemical metabolites; nucleic acids; polysaccharides; cellular fragments; etc.

In order to carry out such assays, a wide variety of solid phases may be employed. Examples include but are not limited to solid phases such as beads, magnetic particles, etc. In a preferred embodiment, the solid phase is a bead.

Those of skill in the art will recognize that the field of immunological detection is well-developed and that a plethora of suitable substrates and detection strategies are known that may be utilized in the measurement phase of an immunological assay, so long as exposure of the assay mixture to the substrate results in the production of a detectable, measurable signal.

Likewise, many types of samples exist which may be analyzed advantageously by practicing the methods of the present invention. Examples of samples that may be analyzed by the practice of the present invention include but are not limited to serum, plasma, urine, cerebrospinal fluid, amniotic fluid, saliva, tissue extracts, etc.

Figure 5:
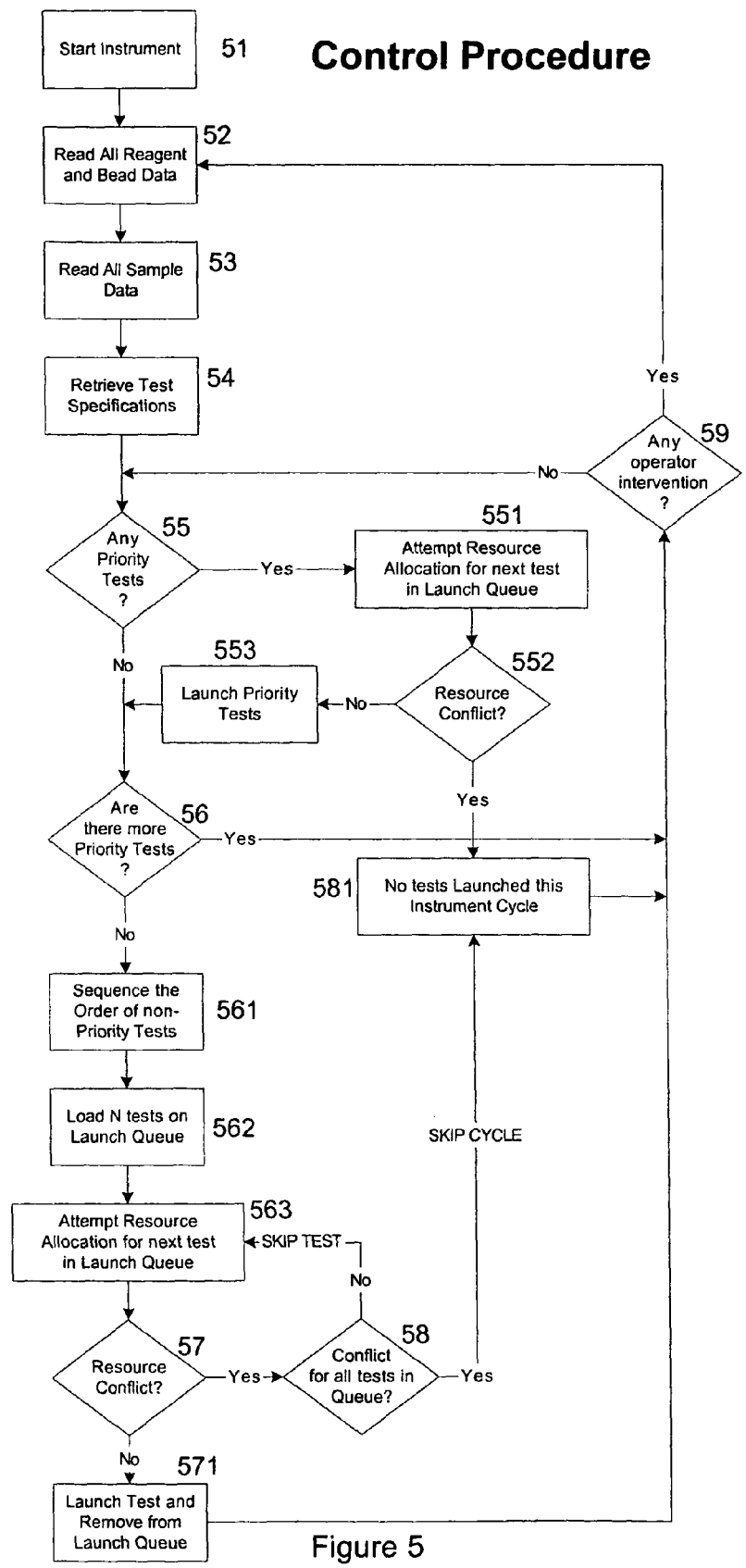
FIG. 5 is a flow chart of the overall control procedure.

Now that the present invention has been described in terms of the assays and the steps within the assays, FIG. 5 describes the flow diagram of the controller for managing these assays. The control procedure begins when a start of test cycle is detected (step 51). Reagents and bead packets have been loaded into the analyzer. The reagent and bead data is read in Step 52. Samples are loaded into the immunoassay analyzer either from the sample storage rack or by an operator and sample data is read is step 53. The samples are read in any number of ways, for example by bar code, RF tagging, etc. The test profiles have been entered by the operator during initialization of the analyzer via the user interface 24. The test profile information is retrieved in step 54 and associated with the samples to be tested. The controller retrieves the test specifications in step 54 which are stored in the storage module 23 and are part of the program parameters 233. Each pending test is described by a vector of variables obtained from program parameters 233. For example, at this stage, the pending tests may be described by the vector: K, P(K), $T_{11}$, $T_{12}$, E which are obtained from the test specifications at step 54. This vector would identify the ID# (K), the assigned path through which the test will proceed (P(K)), incubation times ($T_{11}$ and $T_{12}$) and test profile data (e.g., Pretreat, Dilution, Priority, etc. The priority status is checked at step 55. If the test is determined to be a priority, resource allocation is attempted at step 551. The controller then checks for resource conflicts at step 552 and if no conflicts exist, the test is launched immediately in step 553. If a resource conflict is detected, step 581 prevents a test from being launched in the current cycle. The system then checks for operator intervention at step 59 and then rechecks for priority test back at step 55. Once the priority test is launched, the controller checks for additional priority tests in step 56. If additional priority tests are detected, the controller checks for operator intervention at step 59. If the operator has interrupted the procedure, the controller begins the control procedure again at step 52 and rereads all reagent and bead information and proceeds again to step 53. Operator intervention may include restocking of the analyzer with consumables (e.g., reagent, beads, water, etc.) or the operator maybe reinitializing some system settings such as changing the saturation thresholds ro anticipate an increase in a number of priority tests to be introduced.

If there are no more priority tests detected, the controller initiates the sequencing algorithm in step 561. The sequencing algorithm will be described in more detail in FIG. 6. Once the sequence for the group of tests is defined, the group of tests (defined as N) are loaded on the launch queue at step 562. For each next test in the launch queue, the controller attempts to perform resource allocation in step 563. The resource allocation is described in more detail in FIG. 7.

The controller checks for resource conflicts in step 57 if no conflicts are detected, step 571 launches the test. The control procedure checks for operator intervention in step 59 and then returns to the start of the procedure at either step 52 in the event of intervention or step 55 if there has not been an operator intervention. If a resource conflict is detected at step 57, the conflict is determined for an individual test or a group of tests in the cycle at step 58. If an individual test causes the conflict, this test is skipped and the controller attempts resource allocation for the next test at step 563. The test is held in the launch queue and rechecked until it can be launched without conflict. If a group of tests cause the conflict as determined in step 58, no test is launched during the test cycle and the procedure returns to the beginning of the procedure.

Figure 6:
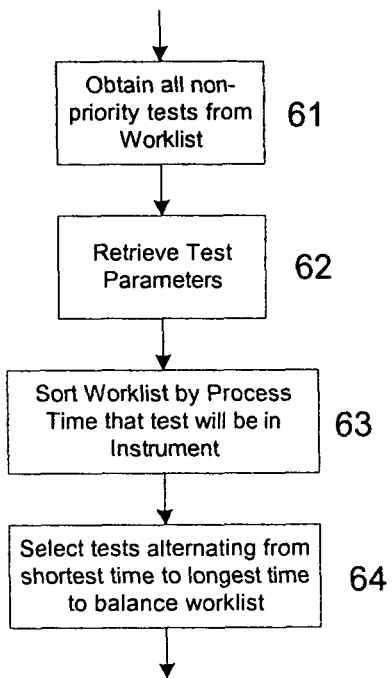
FIG. 6 is a high level flow chart of the Sequencing Algorithm.

FIG. 6 describes the sequencing algorithm. The controller initiates the sequencing algorithm 223 in step 61 (step 561 of FIG. 5). The sequencing algorithm obtains the current resource worklist table (RWL) 231 for the non-priority tests in the instrument. The test parameters such as the ratio of test, the incubation times, pretreatment requirements and dilution levels are retrieved in step 62. The controller updates the RWL 231 to reflect a sequencing strategy such as a test path for each test within the set of waiting tests. Within the program parameters, each assay is associated with a test path that defines the types of resources required to complete the specified test, the order in which these resources need to be accessed, and the time required to complete each test. The sequencing algorithm then sorts the tests by time and resource assignment and updates the RWL 231 with this new sequence in step 63. Tests are ordered for loading on to the launch queue in step 64 by alternating shortest test time with longest test time to balance workload in step 64. The controller then continues the control procedure in step 562 of FIG. 5.

At step 563 of the control procedure shown in FIG. 5, the resource allocation and conflict resolution is performed. This process is described here in more detail and shown in FIG. 7. The resource allocation and conflict resolution procedure (RCR) checks for availability of those resources that have a fixed time location such as the pipettors, pipettors, detection mechanism, etc in step 71. Those resources that do not have a fixed time location are the incubator chains, the luminometer chains, etc. If a conflict is detected at one of the fixed resources at step 72 the test is not launched and the control procedure moves on to step 57 of FIG. 5.

If a conflict is not detected in the fixed resource, at step 722, the variable time resources are checked. Step 73 determines whether there is a conflict in the variable time resources. If a conflict is detected, step 74 checks increments of the test cycle to determine any 'open' test cycles. In the event an open test cycle is identified, step 741 adjusts the target launch time for the test and returns to the control procedure. If another cycle time cannot be identified, the test is not launched at step 742 and the control procedure moves on to step 57 of FIG. 5. If conflicts have been resolved step 751 of the RCR returns to the control procedure at step 57 of FIG. 5 and the test is launched at step 571. In the event that the conflict was resolved at step 73, the dynamic controller checks the workload of duplicate resources (e.g., wash station, transfer mechanism, etc.) in step 731 and selects the destination resource for the particular tests so as to balance the workload across the duplicate resources.

Figure 7:
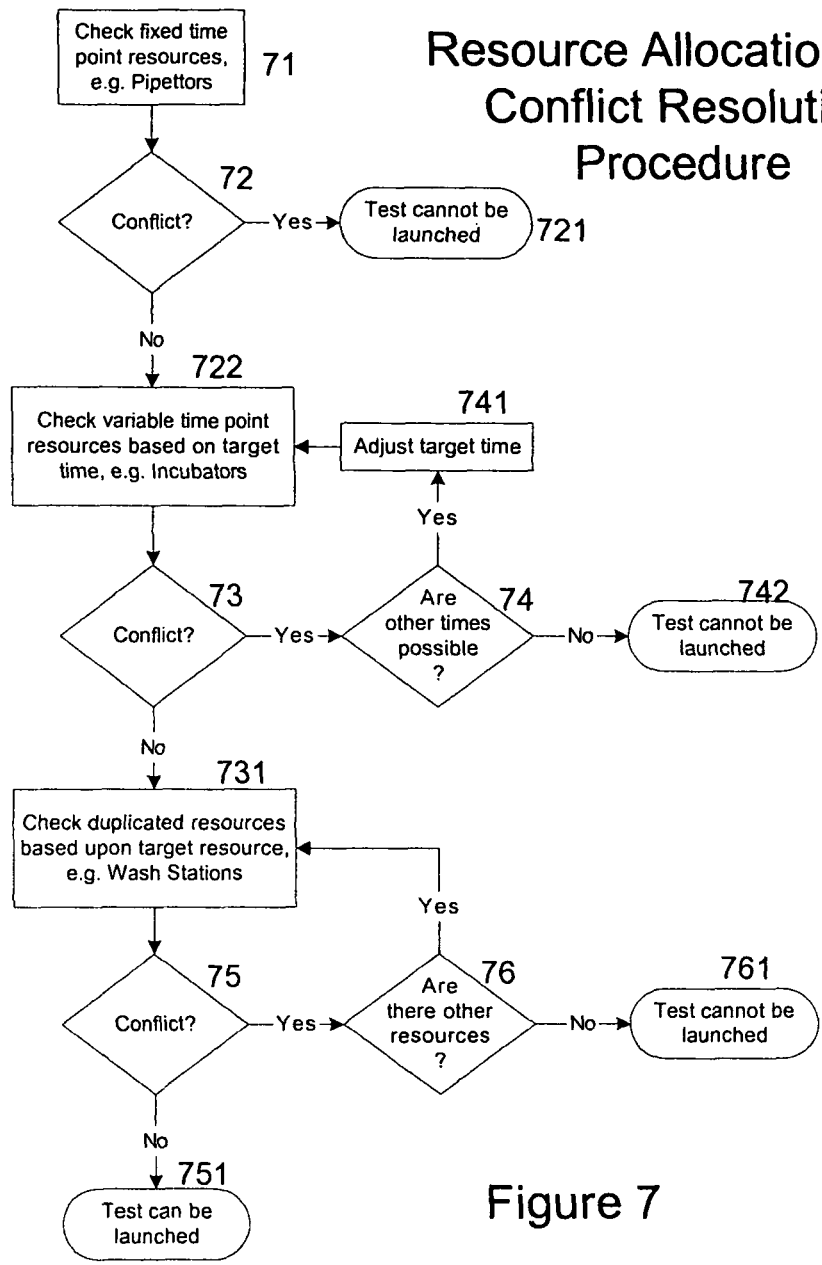
FIG. 7 is a high level flow chart that depicts the resource allocation and conflict procedure.

As part of the determination of resource availability queried throughout the control procedure such as in step 722 of FIG. 7, a saturation threshold for the test resources is set. That is, the maximum number of samples that can be present within the analyzer at any one time. This number can be based on the actual physical limitations of the number of slots (sample vessel holders) in the incubation chains. This maximum threshold may also be set at some number less than the maximum physical level as would be preferable for handling STAT tests (high priority tests). The dynamic controller of the present invention, allows the resource saturation level to be set in a variety of ways. In order to allow higher priority tests to be launched without halting samples currently under test, some resources must be available at all times to introduce the high priority tests into the instrument. That is, some sample vessel holder slots are held vacant and unavailable to non-priority tests so as to allow immediate launching of the priority tests.

Figure 8:
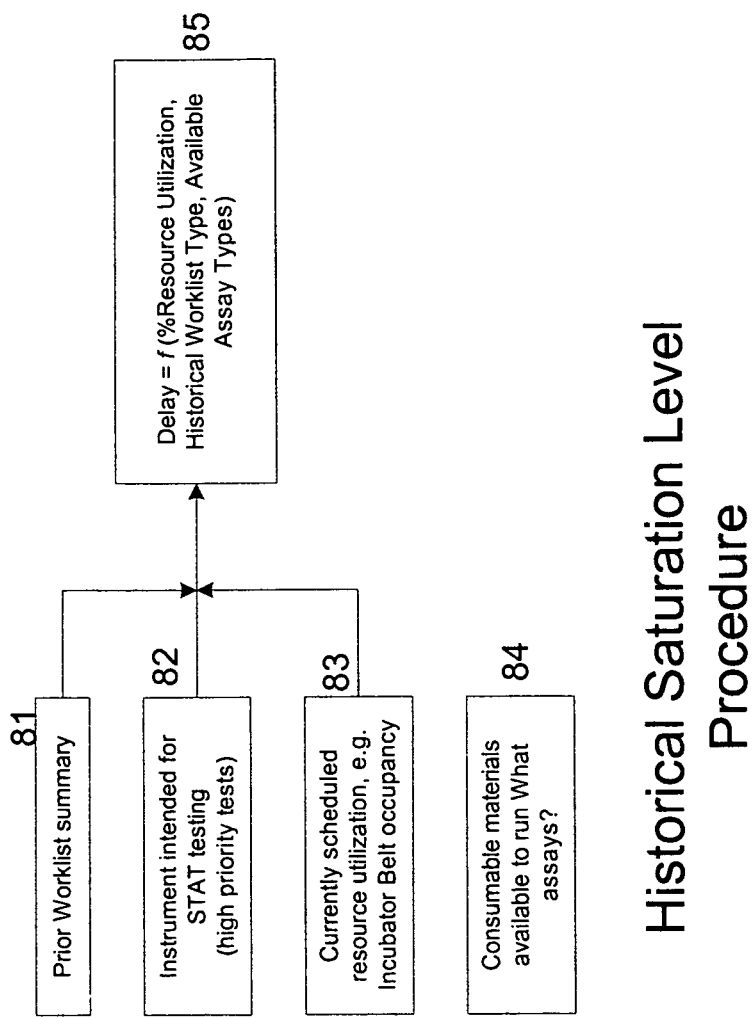
FIG. 8 is a detailed flow diagram of an example resource allocation procedure.

This vacancy ratio, called saturation threshold, can be enabled or disabled by the operator at initialization of the analyzer. This threshold could also be modified by the controller in the event that a large number of priority tests are anticipated suddenly. The present invention has a further capability of setting saturation thresholds based on historical data. That is, the controller can adapt the saturation threshold of the instrument using data that was 'learned' over time. FIG. 8 shows the data analyzed to integrate this capability into the resource allocation and conflict resolution procedure. Within step 73 of FIG. 7, the controller checks variable time resources for availability. As part of this checking, historical data is analyzed. The analysis of the historical data draws on the worklist summary of priority tests (block 81), current resource utilization relative to physical capacity (block 83), consumable quantities (block 84) and the resources needed for the intended high priority tests (block 82). This data is used to create a saturation threshold (block) which delays test launch to allow additional variable time resource openings (or increases launches in the event of decreased need for high priority tests).

EXAMPLE

To more fully understand the dynamic controller of an immunoassay analyzer the preferred embodiment is described with respect to a specific example. This example is discussed as to the steps the dynamic controller would implement associated with a detailed resource allocation flow chart. The example is also described relative to how the controller would manage a test sample through the physical resources within an immunoassay analyzer. These examples are provided for information purposes only and are not to be construed as the only embodiment of the subject invention.

Figure 9:
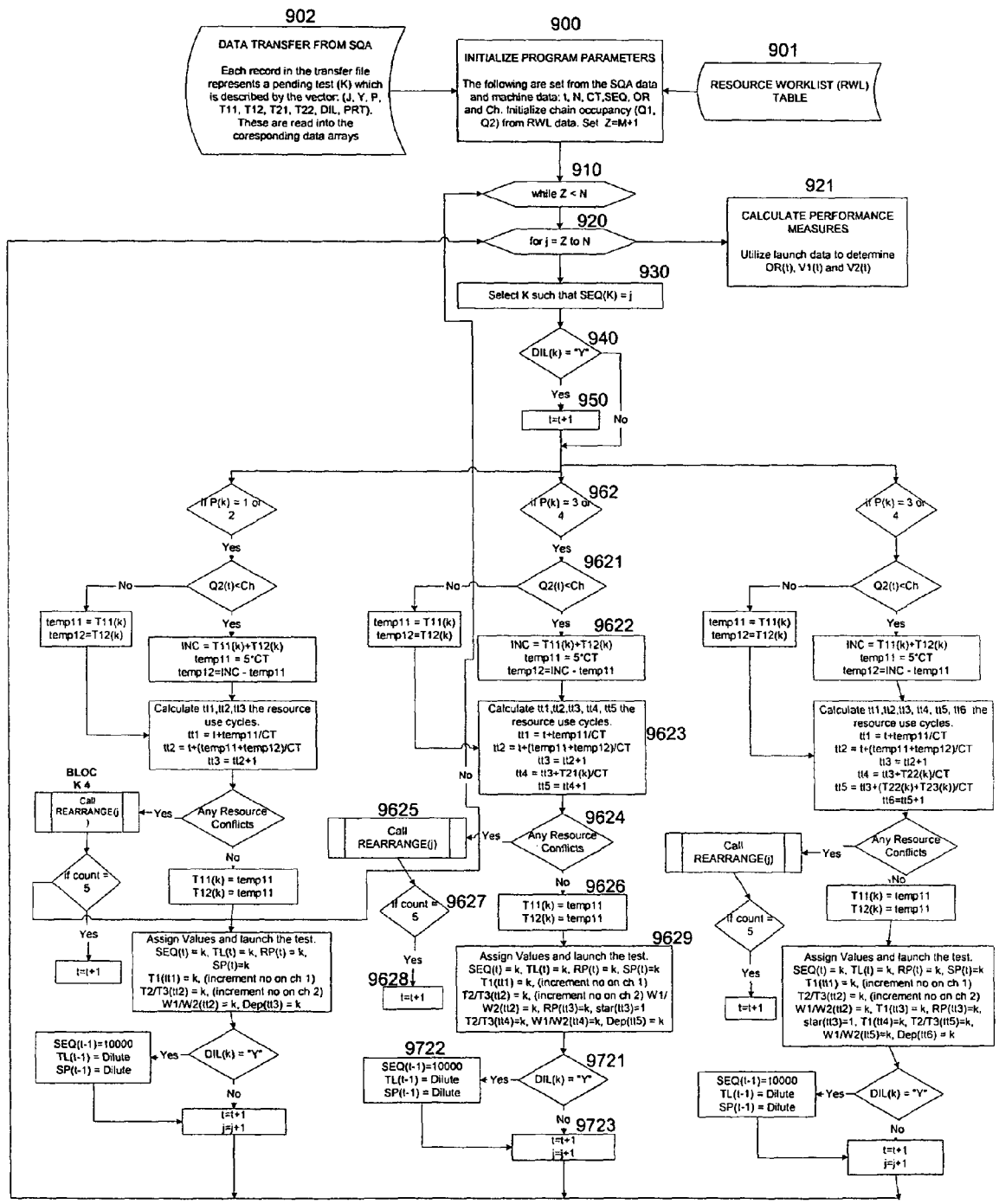
FIG. 9 is a detailed flow diagram for an example resource allocation procedure.

Referring now to FIG. 9 which shows a detailed flow diagram of an example resource allocation procedure, each test to be launched is described by a vector (see step 54 of FIG. 5). Step 600 sets the test vector from the program parameters from the resource workload table. In step 910, the controller checks that the number of tests waiting to be launched is less that the number of tests originally in the launch queue. At step 920, the controller determines that all tests have not been completed, that is the sample for tests (j) is between the maximum number of tests to be launched (N) and the number of tests left to launch (Z). The test is assigned a sequence number as it is launched (SEQ(k)=j) at step 930. The controller queries for DIL status from the tests vector (DIL(K)=Y?). If the test is to be diluted, the test is scheduled for a dilution cycle (t=t+1) at step 950. If no dilution is required, the controller does not allocate the dilution resource. At this point, the controller determines the path which the test same will follow based on the specific assay test profile from the program parameters in step 962. The controller can identify particular paths for each test vessel to follow, for example purposes, the paths are designated as 1, 2, 3 or 4. This is not to be construed as limiting the subject invention to having 4 paths but rather just that a set of paths can be defined relative to particular requirements of the selected assays.

Depending upon which path is designated for the test type, the controller resource allocation continues to step 9621 where the number of available slots on the incubator chain is checked for availability. This availability is dependent upon physical and saturation thresholds of the incubator chain that was discussed previously. The incubation scenario is then defined by the controller in step 9622. That is, the incubation time can be assigned for each test vessel. Step 9623 calculates the number of test cycles required to meet the incubation time duration. Once the incubator time requirements are defined, the controller, in step 9624 checks for resource conflicts. In the event of a conflict, the resource conflict resolution algorithm would be called in step 9625 to increment the test sequence and/or skip a test so as to resolve the conflict. The conflict resolution procedure skips 5 test in the launch sequence queue in step 9627 and checks again for resource conflicts, if no conflicts are detected, the next test is selected and the procedure continues, if a conflict is still detected, the test is skipped in step 9722 and is moved back in the launch queue.

Assuming a conflict is not selected, the actual test resources are allocated in step 9629. These resources include but are not limited to the designated incubation belt slot, the specific wash station, the particular luminometer belt slot, pipettor assignment, etc. Step 9721 sets the dilution control and step 9722 identifies the dilution concentration. once all the test resources are allocated and the allocation has been checked so that there are no conflicts, the test is launched. The controller then increments the test cycle counter and the test sequence counter (t=t+1, j=j+1) and continues the control procedure.

Figure 10:
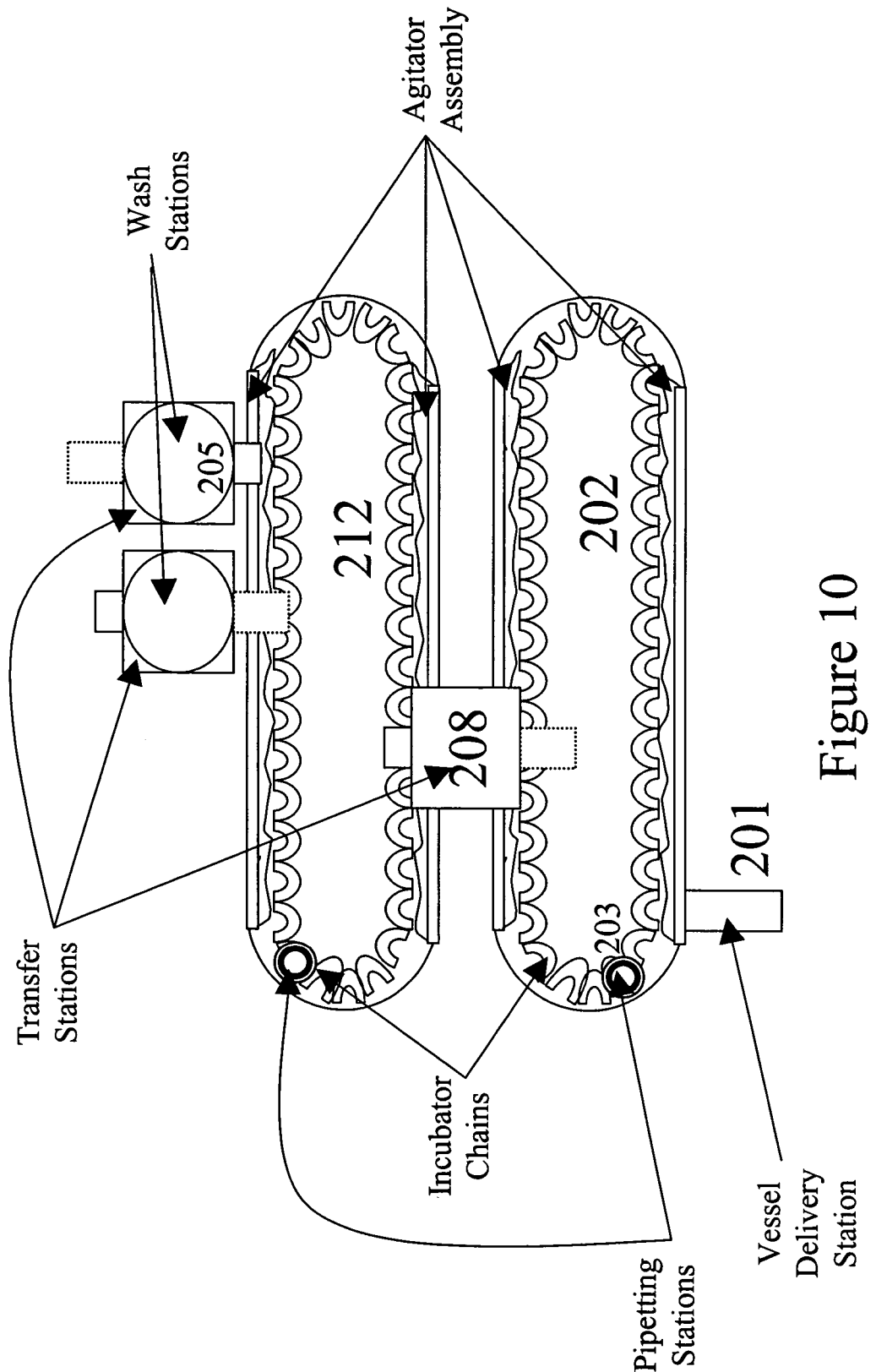
FIG. 10 is a block diagram of a multipath incubator.

Turning now to FIG. 10, once the test sequence is defined and the resource allocation is assigned, the test is launched. A test vessel is presented to the multipath incubator at the vessel delivery station 201. The test vessel may contain a solid phase reagent or may be empty. The test vessel is moved along a transporter device such as the incubator chain 202. On the incubator chain 202, the test vessel is positioned so that it is centered over the chain in order to eliminate variation of speed as the vessel travels around corners. The test vessel is moved to a pipetting station 203 where liquid is added. The liquid that is added may include biological sample (e.g., blood, plasma, urine, etc.), or diluted biological sample, or liquid reagent. The type and quantity of the added liquid is dependent upon the type of assay being performed. The test vessel is moved around the incubator chain 202 for a period of time specified in the program parameters 223 for the individual assay. That is, the amount of time the test vessel is in the incubator chain 202 depends on the tests being performed therein, and the controller (not shown in FIG. 10) controls the progress of each test vessel in the incubator chain 202. As the test vessel is moved along the incubator chain 202, the test vessel is agitated by one or more agitator assemblies 204. The agitator assembly 204 is described in more detail in U.S. Pat. Nos. 7,175,334 and 8,215,821 "Vessel Agitator Assembly." The test vessel progresses around the incubator chain 202 until it is scheduled by the controller to enter a wash station 205 or a transfer station 206. As noted above, the incubator chain 202 may maintain some number of vessels holds empty (saturation level) in order to accommodate STAT tests.

Preferably, there is at least one wash station 205 associated with the incubator chain 202. As discussed above, the controller will seek to balance the workload between identical wash stations 205 in order to both maximize throughput but also to assure that both resources have similar maintenance schedules. In addition, one or more transfer stations 208 may be associated with the incubator chain 202, depending on the overall incubator design. In the event that there are multiple incubator chains, the sample vessel may be moved from incubator chain 202 to incubator chain 212 by the transfer device 208. From incubator chain 212, the sample vessel may be transferred to the wash station 205. The purpose of a dedicated wash station is to remove the reaction liquid supernatant while retaining the solid phase reaction components, add a wash liquid (e.g. water), remove the wash liquid, etc., thus repeatedly washing the solid phase, and then to return the test vessel to the incubator belt from which it was removed. The purpose of a dedicated transfer station is to move a test vessel from an incubator belt to another location, such as to another incubator belt (in a system with two or more belts) or to a luminometer. In some embodiments of the invention, a wash and transfer station are combined, i.e., a test vessel it transferred into the wash station and the solid phase component of the reaction is washed, and then the test vessel is moved (transferred) out of the wash station to a location other than the incubator belt from which it was removed, e.g. to a different incubator belt or to a luminometer subsystem. When the configuration includes two or more duplicate resources, such as wash stations or transfer devices, the controller manages the workload of each duplicate device to so as to balance the amount of work performed by each device.

Once the assay is complete, the next step is to read the result. The test vessel is shuttled to a luminometer. The luminometer and its operation are described in more detail in U.S. Pat. No. 7,951,329.

Figure 11:
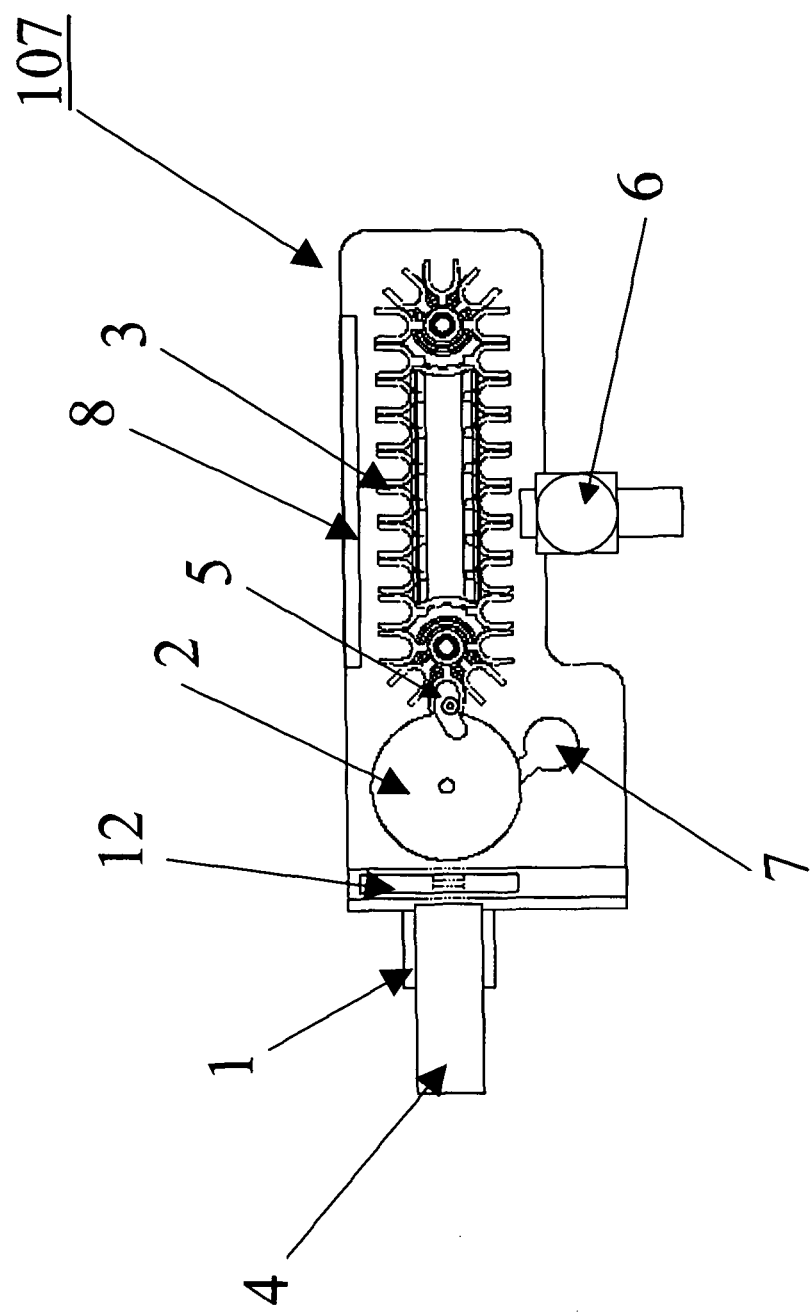
FIG. 11 is a block diagram of a luminometer subsystem.

FIG. 11 shows a more detailed view of luminometer subsystem. The test vessel is transferred to the luminometer subsystem 107 after a wash operation is performed. The transfer device 6 loads the test vessels 5 onto the luminometer chain 3. The luminometer chain 3 rotates in either a clockwise or counterclockwise direction as directed by the controller. A substrate and/or chemical reagent is added to the test vessel 5 and the test vessel 5 is moved along the luminometer chain 3 and shaken by the agitator 8.

The agitator 8 is described in more detail in U.S. Pat. Nos. 7,175,334 and 8,215,821, Vessel Agitator Assembly; however, it should be understood that this invention can be used in combination with a variety of devices that agitate vessels that are present in vessel transportation assemblies. In short, preferably as the vessels pass by the bumps on the agitator 8, the vessels contact the agitator 8 and are essentially "bumped" or agitated. When commanded by the controller, the test vessel 5 is transferred to the read station 2. While in the read station 2, the test vessel is read by the detection mechanism 4 and then discarded to the exit chute 7. In order to protect the detection mechanism 4 from exterior light, the detection mechanism 4 is connected to the read station 2 through a sealed sleeve 1. The sleeve 1 allows the optional attenuation disk 12 to move relative to the read station 2 while preventing exterior light from entering the detection mechanism 4.

One of the important advantages of this configuration is that the read station 2 and luminometer chain 3 are separate. This allows each of the plurality of vessels loaded into the luminometer subsystem 107 to remain on the chain for variable lengths of time. That is, in the preferred embodiment, the test vessels are not required to be serially fed one after another to the read station 2. By using the preferred embodiment that comprises separate mechanisms for transporting the test vessels and for reading the test vessels, test vessels can be agitated while one of the test vessels is being read. Rather, based on the test being performed in a particular test vessel, the test vessel may remain on the chain for shorter or longer time periods as directed by the controller. Some tests may optimally require longer periods between the time when a chemical agent that will be cleaved by bound material on the bead to produce chemiluminescence, phosphorescence, fluorescence or color change is added to the vessel relative to the time when the detection mechanism 4 detects the chemiluminescence, phosphorescence, fluorescence or color change. In addition, some tests may be prioritized for patient care reasons, and will proceed at a faster rate from the luminometer chain 3 to the detection mechanism 4. Thus, preferably, the controller is programmed to control the order of when a test vessel 5 is transferred between the luminometer chain 3 to the read station 2, and it can accomplish this control by tracking the location of the test vessel 5 in the luminometer chain 3. Hence, every test vessel 5 essentially has its own timed interval in the luminometer chain 3, and this timed interval can be controlled based on the test being performed, the other test vessels 5 that are present in the luminometer chain 3, as well as by a prioritization scheme or according to other directives.

Figure 12:
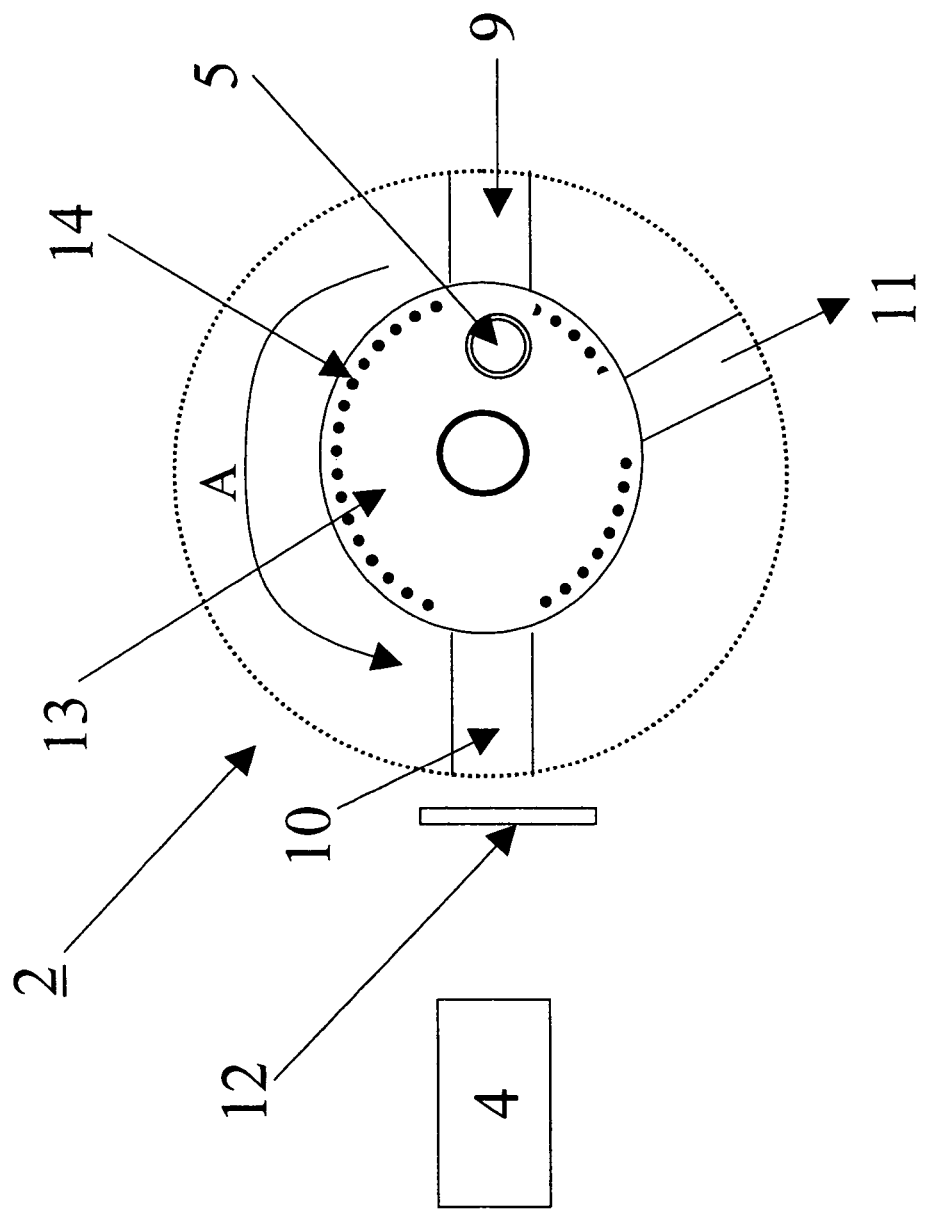
FIG. 12 is a diagram of a test vessel read station.

FIG. 12 shows the progress of the test vessel 5 within the read station 2. The test vessel 5 enters the read station 2 from the luminometer chain 3 at entry position 9. The test vessel 5 is preferably rotated in the counterclockwise direction shown by arrow A around to read position 10. While at read position 10, the test vessel 5 is read by the detection mechanism 4 (e.g., a Photomultiplier Tube (PMT) in the preferred embodiment).

The detection mechanism 4 is protected from exterior light leakage by a sleeve 1 (shown in FIG. 2), a housing 13 and a shield 14 that is part of the luminometer subsystem.

Another important advantage of the invention having a separate read station 2, and luminometer chain 3, is the improved ability to shield the test vessel 5 undergoing detection. This prevents crosstalk from adjacent vessels or ambient radiant energy from adversely impacting on the measurement. The detection mechanism 4 (e.g., Photomultiplier Tube (PMT) is highly sensitive to exterior light. The preferred detection mechanism 4 is described by U.S. Pat. No. 5,316,726.

Although FIG. 3 shows the read station 2 rotating in the counterclockwise direction, it is understood that the read station 2 may rotate in either the clockwise or counter clockwise direction.

The duration of time in which the test vessel 5 is present in the read station 2 at read position 10 is preferably managed by the controller and is dependent upon the specific test being performed. It may be desirable to present the same sample to the detection mechanism for multiple read cycles. Once the analyte is read, the test vessel 5 is discarded at the exit position 11.

While the invention has been described in terms of a few preferred embodiments and an example, those skilled in the art will recognize that the invention can be practiced with modification within the spirit and scope of the appended claims.

The invention claimed is:

1. An immunoassay analyzer, comprising:
   means for loading one or more samples into one or more test vessels;
   means for identifying tests to be performed on each of said one or more samples, each of said tests to be performed in a test vessel;
   a plurality of resources, each of said plurality of resources for performing a specified function on a test vessel, each of said tests identified by said means for identifying requiring one or more of said plurality of resources;
   means for moving a plurality of test vessels to and from one or more resources of said plurality of resources; and
   a computer controller which
   (i) tracks a location of each test vessel;
   (ii) controls movement of said test vessels by said means for moving, and
   (iii) determines a path for each test vessel between each resource based on the test identified for said test vessel by said means for identifying, and the tests identified and location for all other test vessels of said plurality of test vessels, and each path requiring one or more of said plurality of resources and movement between said plurality of resources by said means for moving.

2. The immunoassay analyzer of claim 1 wherein said controller determines an optimized launch of test sequence for each sample based on any samples currently under test and any samples yet to be tested, said launch of test sequence controlling a time and order for tests to be launched.

3. The immunoassay analyzer of claim 2 further comprising a means for setting one or more resource saturation levels, and wherein said computer controller considers said one or more resource saturation levels in the determination of said launch of test sequence.

4. The immunoassay analyzer of claim 3 further comprising means for modifying said one or more resource saturation levels.

5. The immunoassay analyzer of claim 4 wherein said means for modifying said one or more resource saturation levels uses historical information of tests performed previously in the immunoassay analyzer.

6. The immunoassay analyzer of claim 1 wherein said path determined by said computer controller is determined each time a new test is to be performed on said one or more samples.

7. The immunoassay analyzer of claim 1 wherein said path determined by said computer controller considers tests in one or more test vessels which are to be given priority over tests identified for all other test vessels.

8. The immunoassay analyzer of claim 3 wherein said path determined by said computer controller is determined each time a new test is to be performed on said one or more samples.

9. The immunoassay analyzer of claim 1 wherein said path determined by said computer controller reduces a total time period to perform each of the tests of each of said plurality of test vessels relative to a time period required for performing each test sequentially.

10. The immunoassay analyzer of claim 1 wherein said computer controller resolves one or more conflicts in resource allocation by selecting a group of next tests and shifting said group of next tests at least one test cycle until said one or more conflicts is resolved.

11. The immunoassay analyzer of claim 1 wherein said computer controller manages allocation of said one or more resources to balance a workload across a set of duplicate resources of said one or more resources.

12. The immunoassay analyzer of claim 11 wherein said set of duplicate resources includes duplicate wash stations.

13. An automated method for performing immunoassays in an automated immunoassay analyzer, comprising the steps of:
   loading one or more samples;
   identifying tests to be performed on each of said one or more samples, each of said tests to be performed in a test vessel;
   using a computer controller to control movement of a plurality of test vessels to and from one or more resources of a plurality of resources, each of said plurality of resources for performing a specified function on a test vessel, each of said tests identified by said means for identifying requiring one or more of said plurality of resources;
   using a computer controller to track a location of each test vessel;
   using a computer controller to determine a path for each test vessel between each resource based on the test identified for said test vessel by said means for identifying, said location of each test vessel, and the tests identified for all other test vessels of said plurality of test vessels, and each path requiring one more of said plurality of resources and movement between said plurality of resources; and
   moving each of said plurality of test vessels along its respective path determined in said using a computer controller to determine step.

14. The method of performing immunoassays as recited in claim 13 further comprising the step of using a computer controller to determine a launch of test sequence for each test based on samples under tests and samples to be tested, said launch test sequence controlling a time and order of tests to be launched.

15. The method of performing immunoassays as recited in claim 13 further comprising the step of determining one or more resource saturation levels for said launch of test sequence.

16. The method of performing immunoassays as recited in claim 15 further comprising the step of modifying said one or more resource saturation levels.

17. The method of performing immunoassays as recited in claim 16 further comprising the step of using historical information of tests performed previously in said immunoassay analyzer in said modifying step.

18. The method of performing immunoassays as recited in claim 13 wherein said determining and moving step are performed so as to reduce a total time period to perform each of the tests of each of said plurality of test vessels relative to a time period required for performing each test sequentially.

19. The method of performing immunoassays as recited in claim 13 further comprising the step of resolving one or more conflicts in resource allocation by selecting a group of next tests and shifting said group of next tests at least one test cycle until said one or more conflicts is resolved.

20. The method of performing immunoassays as recited in claim 13 further comprising the step of managing allocation of said one or more resources to balance a workload across a set of duplicate resources of said one or more resources.

* * * * *